United States Patent [19]

Skakoon et al.

[11] Patent Number: 5,156,598
[45] Date of Patent: Oct. 20, 1992

[54] PREFILLED SYRINGE DELIVERY SYSTEM

[75] Inventors: James G. Skakoon, Melrose; Steven E. Kern, Somerville; William V. Lombardi, Northboro, all of Mass.

[73] Assignee: C. R. Bard, Inc., Murray Hill, N.J.

[21] Appl. No.: 749,615

[22] Filed: Aug. 19, 1991

Related U.S. Application Data

[63] Continuation of Ser. No. 280,368, Dec. 6, 1988, abandoned.

[51] Int. Cl.$^5$ .............................................. A61M 5/32
[52] U.S. Cl. ............................................ 604/192; 604/86; 604/411; 604/905; 604/283
[58] Field of Search ................... 604/83, 86, 88, 192, 604/198, 243, 254, 263, 283, 272, 905, 411, 403

[56] References Cited

U.S. PATENT DOCUMENTS

| | | | |
|---|---|---|---|
| 1,432,238 | 10/1922 | Eisele . | |
| 2,999,499 | 9/1961 | Willet | 604/83 |
| 3,128,765 | 4/1964 | Tint | 604/228 |
| 3,332,418 | 7/1967 | Brody . | |
| 3,378,006 | 4/1968 | Burke . | |
| 3,401,693 | 9/1968 | Cohen . | |
| 3,557,787 | 1/1971 | Cohen . | |
| 3,889,673 | 6/1975 | Povey et al. | 604/192 |
| 3,896,508 | 10/1976 | Berrington | 604/905 X |
| 3,918,450 | 11/1975 | Patel | 604/243 |
| 4,022,205 | 5/1977 | Tenczar | 604/905 X |
| 4,116,196 | 9/1978 | Kaplan et al. | 604/192 |
| 4,232,669 | 11/1980 | Nitshke | 604/192 |
| 4,328,802 | 5/1982 | Curley et al. | 604/88 |
| 4,329,989 | 5/1982 | Dallons . | |
| 4,445,896 | 5/1984 | Gianturco | 604/238 |
| 4,504,265 | 3/1985 | Rudzena | 604/86 |
| 4,511,359 | 4/1985 | Vaillancourt | 604/411 |
| 4,534,758 | 8/1985 | Akers | 604/85 |
| 4,535,820 | 8/1985 | Raines | 137/854 |
| 4,540,027 | 9/1985 | Forberg | 137/848 |
| 4,556,086 | 12/1985 | Raines | 604/247 |
| 4,563,173 | 1/1986 | Ledley | 604/81 |
| 4,564,054 | 1/1986 | Gustavsson | 604/411 |
| 4,576,211 | 3/1986 | Valentini et al. | 604/88 X |
| 4,585,435 | 4/1986 | Vaillancourt | 604/27 |
| 4,601,703 | 7/1986 | Herlitze | 604/86 |
| 4,631,057 | 12/1986 | Mitchel | 604/192 |
| 4,634,428 | 1/1987 | Cuu | 604/110 |
| 4,643,722 | 2/1987 | Smith | 604/192 |
| 4,643,724 | 2/1987 | Jobe | 604/232 |
| 4,664,653 | 5/1987 | Sagstetter | 604/197 |
| 4,669,463 | 6/1987 | McConnel | 128/207 |
| 4,676,783 | 6/1987 | Jagger et al. | 604/171 |
| 4,681,567 | 7/1987 | Masters | 604/198 |
| 4,693,708 | 9/1987 | Wanderer | 604/198 |
| 4,702,739 | 10/1987 | Milorad | 604/198 |
| 4,723,943 | 2/1988 | Spencer | 604/198 |
| 4,737,144 | 4/1988 | Choksi | 604/198 |
| 4,740,203 | 4/1988 | Hoskins | 604/191 |
| 4,747,829 | 5/1988 | Jacob | 604/110 |
| 4,747,836 | 5/1988 | Luther | 604/198 |
| 4,752,292 | 6/1988 | Lopez et al. | 604/244 |
| 4,759,756 | 7/1988 | Forman et al. | 604/413 |
| 4,772,271 | 9/1988 | Meyer | 604/184 |
| 4,772,272 | 9/1988 | McFarland | 604/198 |
| 4,834,716 | 5/1989 | Ogle | 604/192 |
| 4,850,978 | 7/1989 | Dudar et al. | 604/201 |
| 4,904,244 | 2/1990 | Harsh et al. | 604/187 |
| 4,932,944 | 3/1988 | Jagger et al. | 604/191 |
| 4,943,281 | 7/1990 | Kothe | 604/192 |
| 4,946,445 | 8/1990 | Lynn | 604/192 |
| 4,950,260 | 8/1990 | Bonaldo | 604/283 |
| 4,952,210 | 8/1990 | Alchas | 604/251 |
| 4,969,876 | 11/1990 | Patterson | 604/171 |
| 4,981,469 | 1/1991 | Whitehouse et al. | 604/86 |
| 4,998,925 | 3/1991 | Al-Sioufi et al. | 604/283 |

FOREIGN PATENT DOCUMENTS 8910770  11/1989  World Int. Prop. O. ......... 604/192

Primary Examiner—John D. Yasko
Assistant Examiner—Mark O. Polutta
Attorney, Agent, or Firm—Kane, Dalsimer, Sullivan, Kurucz, Levy, Eisele, and Richard

[57] ABSTRACT

A prefilled syringe with a permanent cylindrical needle guard extending beyond the tip of the needle is disclosed. The needle guard is integral with the syringe holder so as to provide no exposure, selective or otherwise, of the needle. A removable needle guard is further provided. A tubing set is provided with a puncture port which fits in a liquid-tight manner into the cylindrical needle guard. The tubing set further includes anti-siphoning means and low volume tubing.

6 Claims, 2 Drawing Sheets

PREFILLED SYRINGE DELIVERY SYSTEM

This is a continuation of copending application(s) Ser. No. 07/280,368 filed on Dec. 6, 1988, now abandoned.

BACKGROUND OF THE INVENTION

1. Field of the Invention

The present invention relates, in general, to an integrated delivery system using a prefilled syringe. In particular, the present invention relates to the use of a permanently protected needle in such a system.

2. Description of the Prior Art

In the art of medical syringes, it is well known to provide a protected needle which is selectively exposed for a limited period for injection before being returned to a protected state. This protected state of the needle allows the syringe to be easily handled by medical personnel with reduced risk of accidental injury, injection and subsequent infection from an exposed needle. However, such syringes are still hazardous in that they may be mishandled by medical personnel so that a needle is inadvertently exposed leading to the possibility of such accidental injury, injection and infection.

Examples of these syringes are shown in U.S. Pat. Nos. 4,693,708 and 4,681,567. The 4,693,708 patent discloses a cylindrical housing of the needle guard which extends and retracts with respect to the syringe barrel. The 4,681,567 patent discloses a slidably mounted sheath which acts as a needle guard.

Moreover, it is well-known in the prior art to use a sealed hypodermic syringe. An example of such a syringe is found in U.S. Pat. No. 3,825,003.

Further, in the prior art, it is well known to use a prefilled syringe to deliver medicine or pharmaceutical product to separate medical apparatus for subsequent infusion into the patient. However, in order to be compatible with a wide range of apparatus, and possibly due to an ill-considered decision to borrow from the art of syringes which are used for direct injection into a patient (which fundamentally must provide an exposed needle to allow for direct injection), these prefilled syringes have typically included a needle which is either permanently exposed or selectively exposed.

This permanent or selective exposure of the needle leads to two disadvantages.

Firstly, the exposed needle is dangerous to medical personnel.

Secondly, the exposed needle typically has no means for guiding the needle into a small insertion area of the aforementioned separate medical apparatus. Inaccurate insertion of the needle into the medical apparatus can result in contamination of the needle, damage to the needle or to the apparatus or injury to the user. A good example of such an apparatus is disclosed in U.S. Pat. No. 4,232,669. This apparatus includes a needle which is protected by a protective sheath and a removable protective cap. In order to use this device, the cap is removed which exposes the needle beyond the protection of the detachable protective sheath.

It is therefore an object of the present invention to provide a prefilled syringe wherein the needle is permanently shielded.

It is therefore a further object of the present invention to provide a prefilled syringe which includes a means for guiding the needle accurately into other medical apparatus.

SUMMARY OF THE INVENTION

The present invention is a prefilled syringe delivery system which includes a prefilled syringe with a needle permanently protected by a cylindrical guard which extends beyond the tip of the needle. The open end of the cylindrical guard serves as a guide for a puncture port to be accurately positioned with respect to the needle.

The puncture port leads to tubing which includes an anti-siphoning means and means for connection to other apparatus.

DETAILED DESCRIPTION OF THE PREFERRED EMBODIMENT

Figure 1:
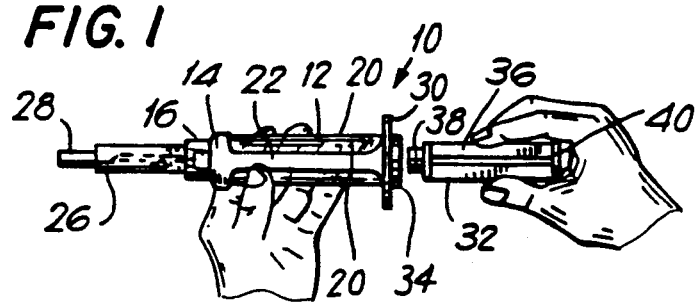
FIG. 1 discloses a side plan view of the prefilled syringe with the plunger at its withdrawn position, the piston screwably removed from the plunger, and a needle sheath over the needle.
Figure 2:
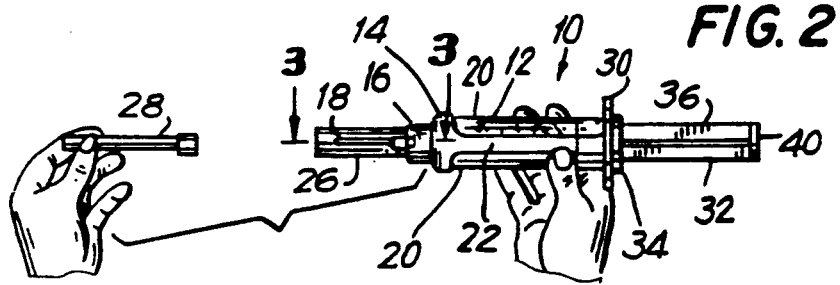
FIG. 2 discloses a side plan view of the prefilled syringe with the plunger at its withdrawn position, the piston screwably inserted into the plunger and the needle sheath removed.

Referring now to the drawings in detail wherein like numerals refer to like elements throughout the several views, apparatus 10 is disclosed in FIGS. 1 and 2.

Syringe 12, which contains the pharmaceutical product, is held within syringe holder 14. Syringe 12 is preferably made of breakage resistant glass while syringe holder 14 is made of plastic or some similar material which is resistant to breakage. Needle hub 16 is attached to syringe 12 and, in turn, is attached to needle 18 (See FIG. 3). The connections between syringe 12 and hub 16 and between hub 16 and needle 18 are, of course, liquid-tight.

The syringe holder 14 engages the outer curved cylindrical surface of syringe 12 with open portions 20 separated by a stem 22 in the intermediate portion thereof. This allows the user to grasp firmly either the syringe 12 or the syringe holder 14.

Figure 3:
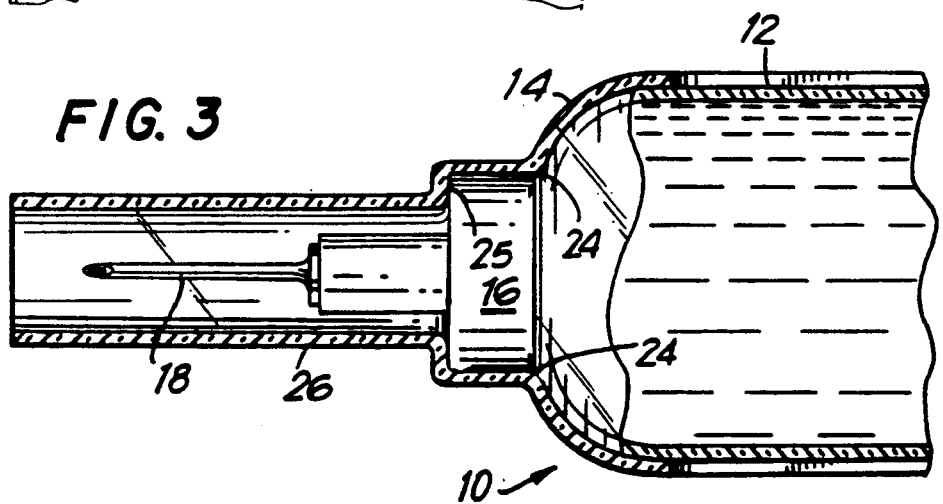
FIG. 3 discloses a cross-sectional view along section 3—3 of FIG. 2.
Figure 4:
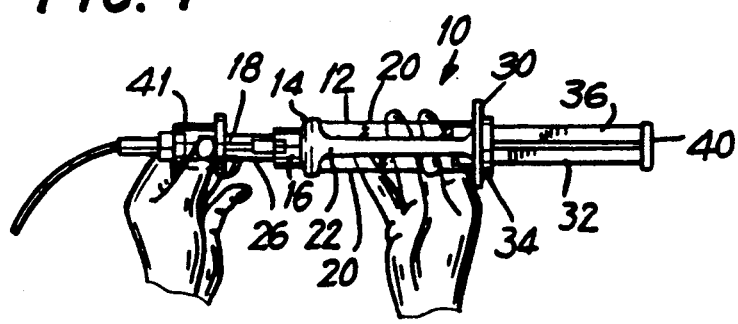
FIG. 4 discloses a side plan view of the prefilled syringe with the puncture port inserted over the needle.

As shown more clearly in FIG. 3, the syringe holder 14 further engages the needle hub 16 with a lip 24 as well as surface 25 which allow the syringe 12 and syringe holder 14 to be rotatable about one another while preventing any longitudinal movement of the syringe 12 with respect to the syringe holder 14.

Needle guard 26 is integrally formed on the proximate end of syringe holder 14 in the shape of a cylinder with the needle 18 as its longitudinal axis. The needle guard 26 extends from the proximate face of needle hub 16 to beyond the tip of a needle 18. Needle 18 is therefore permanently protected and not exposed as needle guard 26 is integral with syringe holder 14 and lip 24 working together with surface 25 prevents any relative longitudinal movement of syringe 12 and syringe holder 14.

Apparatus 10 further includes a needle sheath 28 which covers the needle 18 to provide further safety during transportation (See FIG. 1) but is removed during use (See FIG. 2).

The distal end of syringe holder 14 includes outwardly extending annular flanges 30 which serve as finger grips.

A plunger rod 32 is engaged through the distal end of the syringe 12. Piston 36 is comprised of a rubber plunger 34 and a plunger rod 32. Rubber plunger 34 engages the interior of syringe 12 is a liquid-tight but slidable manner. Plunger rod 32 includes a male threaded portion 38 on its proximate end which engages a female threaded portion (not shown) of rubber plunger 34 and a flat handle portion 40 on its distal end.

The female threaded portion of the rubber plunger 34 allows the plunger rod 32 to be disassembled during transportation, even if apparatus 10 is filled with pharmaceutical product, thereby resulting in a more compact package which is not as susceptible to inadvertent movement and loss of the pharmaceutical product.

Figure 5:
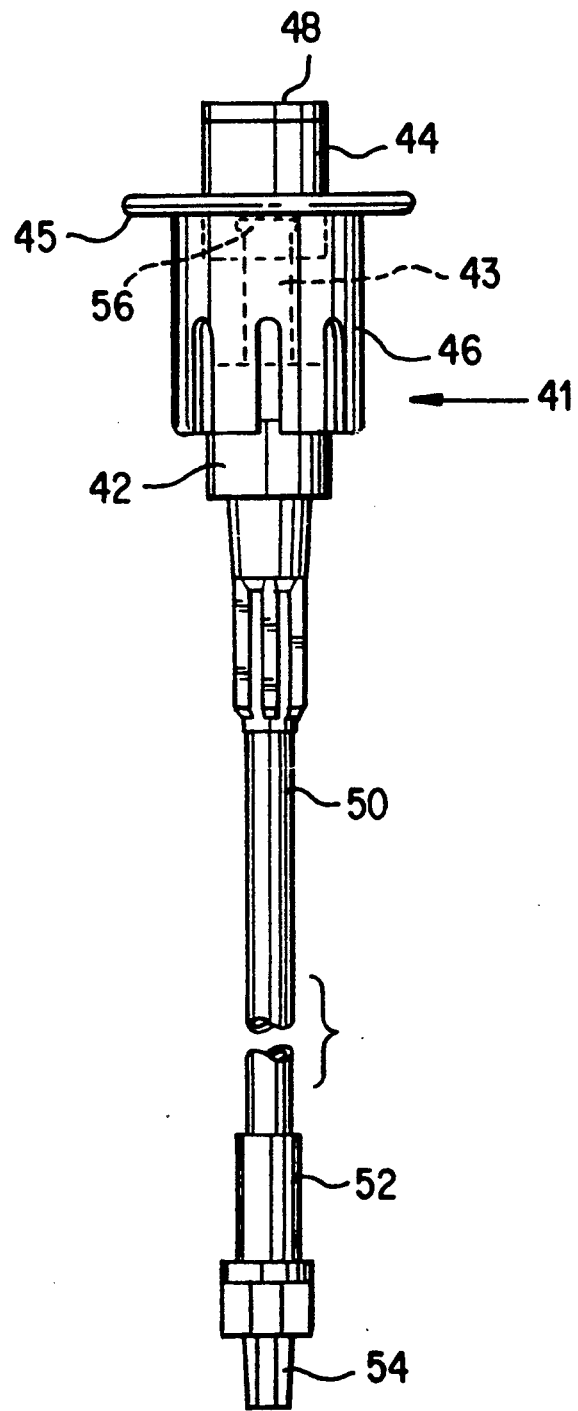
FIG. 5 discloses a side plan view of the tubing set of the apparatus, with a Luer ® (or similar) connector shown in phantom under the puncture port.

In order to use apparatus 10 effectively, tubing set 41 as disclosed in FIG. 5 is supplied. Tubing set 41 includes an anti-siphoning check valve 42, such as is disclosed in U.S. Pat. No. 4,535,820, and an input stem 43 leading to cylindrical input 44. Cylindrical input 44 has a diameter just less than the internal diameter of needle guard 26. During operation, check valve 42 has a positive crack pressure to help prevent uncontrolled syringe emptying. A tamper-resistant disk 45 surrounds anti-siphoning check valve 42 and includes an annular hub 46 which serves as a manual grip for tubing set 41. Disk 46 further forms a mechanical interference with the housing of a syringe pump (not shown) to help prevent tampering or inadvertent disconnection. Cylindrical input 44 includes a rubber puncture port 48 which serves as an injection site and further serves as a sterile connection prior to injection by needle 18. Low volume tubing 50 extends from check valve 42 to a lower Luer ® (or similar) connector 52 which is covered by a protective cap 54. In its preferred embodiment, tubing 50 is ninety-six inches long, resulting in a priming volume of 2.1 milliliters for the tubing set 41. Lower Luer ® (or similar) connector 52 provides a means for attachment to secondary medical devices (not shown) or to a direct injection needle (not shown) for direct infusion into the patient.

The cylindrical input 44 may be screwably removed from anti-siphoning check valve 42 to expose a Luer ® (or similar) lock connector 56 on the end of stem 43 in order to adapt the tubing set 41 to a standard Luer ® (or similar) lock syringe (not shown).

In order to use apparatus 10, the user should firstly be skilled in aseptic technique and accepted IV (intravenous) practice. Syringe 12 is ordinarily provided prefilled with pharmaceutical product or medicine from the manufacturer or from a central location in the medical facility. The user screws plunger rod 32 into rubber plunger 34 so as to form a piston 36. The user removes needle guard 28. The user pushes the piston 36 to expel all air from the syringe 12. The user may wish to use antiseptic to sterilize puncture port 48. The user holds annular hub 46 of disk 45 and guides the cylindrical input 44 and puncture port 48 of tubing set 41 into the interior of needle guard 26. Further, as cylindrical input 44 and puncture port 48 are positioned in needle guard 26 prior to insertion of needle 18 through puncture port 48, needle 18 is accurately positioned against puncture port 48 prior to insertion. When needle 18 is inserted through puncture port 48, a liquid-proof engagement is formed between apparatus 10 and tubing set 41. The user removes protective cap 54 from lower Luer ® connector 52 and lower Luer ® connector is connected to either a direct injection needle (not shown) or to another medical device (not shown). The user pushes the piston 36 to expel all air from the syringe 12 and tubing set 41. The user inserts the syringe holder 14 and piston 36 into a medical pump (not shown) and makes the appropriate connection to the patient. The user then activates the medical pump.

In some rare applications not involving direct infusion into patients, the user may dispense with the medical pump and use piston 36 to manually inject the medicine or pharmaceutical product into another medical device (not shown).

Thus the several aforementioned objects and advantages are most effectively attained. Although a single preferred embodiment of the invention has been disclosed and described in detail herein, it should be understood that this invention is in no sense limited thereby and its scope is to be determined by that of the appended claims.

What is claimed is:

1. An apparatus comprising:
    a syringe including a needle, a barrel, and a plunger axially slidable within said barrel;
    a syringe holder engaging substantially an entire longitudinal length of said barrel of said syringe;
    a substantially cylindrical needle guard extending from said syringe beyond the tip of said needle and having an interior diameter and an exterior diameter, said needle guard being formed integrally with said syringe holder;
    a tubing set including a puncture port means insertable within said needle guard, tubing leading from said puncture port means, an annular hub serving as a manual grip for the tubing set, and a tamper-resistant disk extends radially from the annular hub for forming a mechanical interface with surfaces of a syringe pump to cooperate in preventing tampering; and
    wherein upon gripping said annular hub and interposing and guiding the needle guard between the puncture port means and the annular hub, to thereby engage said puncture of the puncture port means by the needle thereby fluid will then be permitted to be injected from said syringe through said needle and through said tubing set, said puncture port means being removable from said tubing set in order to expose a first lock connector.

2. The apparatus of claim 1 wherein said tubing leads from said puncture port means to a second lock connector.

3. The apparatus of claim 1 wherein said tubing set includes anti-siphoning means between said puncture port means and said tubing.

4. The apparatus of claim 1 wherein said syringe is prefilled.

5. An apparatus comprising:
    a syringe including a needle barrel, and a plunger axially slidable within said barrel;
    a syringe holder engaging substantially an entire longitudinal length of said barrel of said syringe;
    a substantially cylindrical needle guard extending from said syringe beyond the tip of said needle and having an interior diameter and an exterior diameter, said needle guard being formed integrally with said syringe holder;

a tubing set including a puncture port means insertable within said needle guard, tubing leading from said puncture port means, an annular hub serving as a manual grip for the tubing set, and a tamper-resistant disk extends radially from the annular hub for forming a mechanical interface with surfaces of a syringe pump to cooperate in preventing tampering; and wherein upon gripping said annular hub and interposing and guiding the needle guard between the puncture port means and the annular hub, to thereby engage said puncture port means within said needle and then upon puncture of the puncture port means by the needle thereby fluid will then be permitted to be injected from said syringe through said needle and through said tubing set, said tubing set including anti-siphoning means between said puncture port means and said tubing, said puncture port means being removable from said anti-siphoning means in order to expose a first lock connector.

6. The apparatus of claim 5 wherein said tubing leads from said anti-siphoning means to a second lock connector.

* * * * *